US008062208B1

(12) United States Patent
Cannon et al.

(10) Patent No.: US 8,062,208 B1
(45) Date of Patent: Nov. 22, 2011

(54) EROGENIC STIMULATOR WITH LOOP END

(75) Inventors: Catherine Cannon, Mariposa, CA (US); Melissa Mia Kain, Mulberry, FL (US)

(73) Assignees: Catherine Cannon, Mariposa, CA (US); Melissa Mia Kain, Mulberry, FL (US)

( * ) Notice: Subject to any disclaimer, the term of this patent is extended or adjusted under 35 U.S.C. 154(b) by 594 days.

(21) Appl. No.: 12/334,000

(22) Filed: Dec. 12, 2008

(51) Int. Cl.
*A61F 5/00* (2006.01)

(52) U.S. Cl. .......................................................... 600/38

(58) Field of Classification Search ............... 600/38–41
See application file for complete search history.

(56) References Cited

U.S. PATENT DOCUMENTS

D376,650 S 12/1996 Kain ............................ D24/215
D384,156 S 9/1997 Kain ............................ D24/200
D384,158 S 9/1997 Kain ............................ D24/215
5,690,603 A 11/1997 Kain ............................... 600/38
5,853,362 A * 12/1998 Jacobs ............................ 600/38
6,132,366 A 10/2000 Ritchie et al. ................... 600/38
RE38,924 E 12/2005 Ritchie et al. ................... 600/38
7,604,587 B2 * 10/2009 Manska et al. .................. 600/38
2003/0097041 A1 * 5/2003 Ritchie et al. ................... 600/38

* cited by examiner

*Primary Examiner* — John Lacyk
(74) *Attorney, Agent, or Firm* — Robert C. Kain, Jr.

(57) ABSTRACT

The erogenic stimulator may be a two-piece stimulator for use by two partners or may be an erogenic stimulator hanger for a phallic body member. The phallic body member includes a distal end and a proximal base end with one or more radial flange elements. The second member (sometimes referred to as the hanger) has a bulbous proximal end portion, sized for receipt in an anal or vaginal cavity, a U-shaped curved stem leading a distal annulus. The annulus has an opening with a cross-sectional dimension greater than the maximal cross-sectional dimension of the phallic body member. The phallic body member is inserted and hung on the annulus of the U-shaped second member-hanger. The inboard face of the annulus abuts the inboard face of the flange elements of the cylindrical body member.

34 Claims, 6 Drawing Sheets

EROGENIC STIMULATOR WITH LOOP END

The present invention relates to an erogenic stimulator configured as a two-piece system with a first elongated generally cylindrical and phallic body hung in an annulus on a second U-shaped member which U-shaped member has an opposing bulbous end portion or configured as erogenic stimulator hanger wherein the phallic body is hung in an annulus on a second U-shaped member formed as a hanger.

BACKGROUND OF THE INVENTION

This invention pertains to sexual or erogenous stimulation devices in general and, more particularly, to a self-retained device for simultaneous use by two sexual partners such that the erotic areas of both such users are concurrently excited.

GENERAL BACKGROUND

Marital or sexual aids have been known and used throughout the centuries. Generally, such aids have been designed either for self-stimulation or for the stimulation of one party only. However, some aids satisfy two partners at the same time. This latter type of aid or stimulators is designed primarily for use by a female user and often incorporates a flexible phallic shaped stimulator secured to a base. Variations of this type of stimulator include two such phallic shapes linearly secured to opposite sides of a common or intermediate flange. Unfortunately, because of the co-linear nature of these opposite shapes, the simultaneous use of such a device by two partners requires some gymnastic-like maneuvers.

Also, it is common for these devices to not be self-retaining, that is, when one end is retained in the vagina or anal cavity, the other end is free to stimulate the other person. Instead, these devices rely upon a series of straps in order to hold and retain the device in place on one user for proper use on the other person. However, fastening such straps prior to use is cumbersome and discomforting and causes undesirable delay.

U.S. Pat. No. 5,690,603 to Kain discloses a self-retaining stimulator, that is, when one end is retained in the vagina or anal cavity, the other end is free to stimulate the other person. The disclosure of U.S. Pat. No. 5,690,603 to Kain is incorporated herein by reference thereto.

OBJECTS OF THE INVENTION

It is thus an object of the present invention to provide a marital or sexual aid that is capable of simultaneously stimulating the erotic areas of both users.

It is a further object of this invention to provide an aid that is self-retaining such that straps or other holding devices are not required, thereby eliminating any delay and discomfort.

A further object of this invention is to provide a device that is capable of being used by partners of the same sex or of the opposite sex.

Yet another object of this invention is to provide a two-piece aid which may be used separately or coupled together by hanging the cylindrical phallic body on the annulus of the U-shaped member.

SUMMARY OF THE INVENTION

One embodiment of the invention is a two-piece erogenic stimulator for use by two partners. The two-piece model includes a first elongated generally cylindrical and phallic body member with a distal end and a proximal base end. The generally cylindrical body member has a maximal cross-sectional dimension. The proximal base has one or more flange elements extending radially from the generally cylindrical body. The second member of the two-piece set has a bulbous end portion sized for receipt in an anal or vaginal cavity. The second member is generally U-shaped with a curved stem leading from said bulbous end portion to a distal second member end. The distal end of the second member has an annulus which substantially follows or falls within the general U-shape of the second member. The annulus has an opening with a cross-sectional dimension greater than the maximal cross-sectional dimension of the first generally cylindrical body member. The generally cylindrical and phallic body member is hung on the annulus of the U-shaped second member when the members are coupled together by insertion of the cylindrical body member through the annulus. The inboard face of the annulus abuts the inboard face of the flange elements of the cylindrical body member.

The alternative embodiment is an erogenic stimulator hanger used by two persons in combination with an elongated generally cylindrical phallic body. The cylindrical phallic body has a maximal cross-sectional dimension and one or more flange elements extending radially therefrom. The erogenic stimulator hanger is combined with and coupled to the cylindrical phallic body. The erogenic stimulator hanger includes a generally U-shaped member having a bulbous end portion sized for receipt in an anal or vaginal cavity and a curved stem leading from the bulbous end portion to an annulus forming a distal end portion of the generally U-shaped curve. The annulus defines an opening with an open cross-sectional dimension greater than the maximal cross-sectional dimension of the phallic body member such that the phallic body is insertable through the annulus and hangs thereon when an inboard face of the annulus abuts the inboard face of the flange elements.

BRIEF DESCRIPTION OF THE DRAWINGS

Further objects of the present invention can be found in the detailed description of the preferred embodiments when taken in conjunction with the accompanying drawings in which.

DETAILED DESCRIPTION OF THE PREFERRED EMBODIMENTS

The present invention relates to a two piece erogenic stimulator or an erogenic stimulator hanger wherein a phallic body is hung in an annulus on a U-shaped member.

Similar numbers designates similar items throughout the drawings and the specification.

Figure 1:
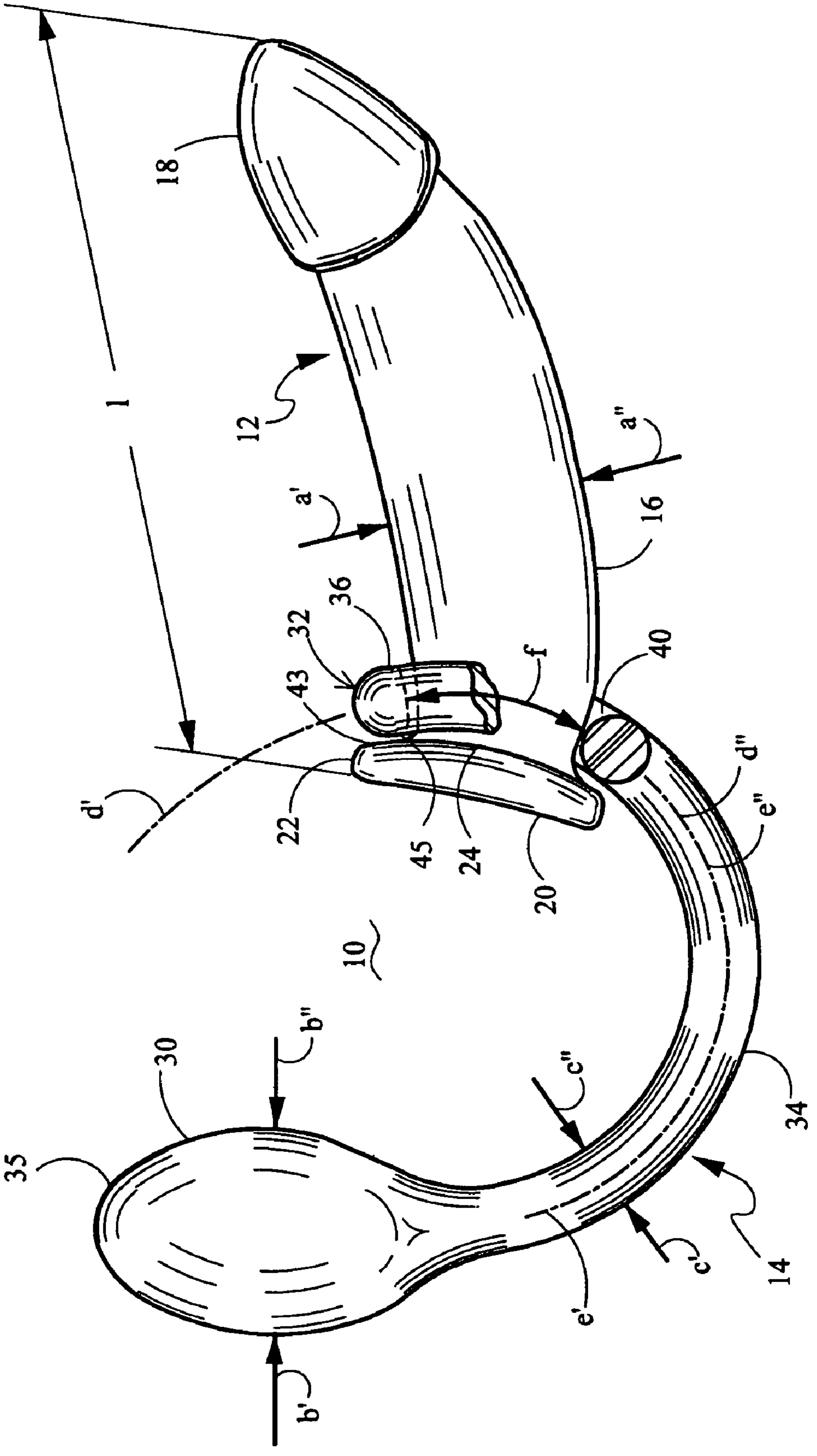
FIG. 1 diagrammatically illustrates an erogenic stimulator aid wherein a first elongated generally cylindrical phallic body member is hung on an annulus of a generally U-shaped second member.

FIG. 1 diagrammatically illustrates a two piece erogenic stimulator 10 which includes a first elongated generally cylindrical phallic body 12 and a second, generally U-shaped member 14. Generally cylindrical phallic body member 12 may be curved or may be designed with a single longitudinal axis. However, as discussed later, the maximal cross-sectional dimension of body member 12 must be smaller than the opening of the annulus or ring at the end of U-shaped member 14. Although the basic concept herein is that maximal cross-sectional dimension of body member 12 must be smaller than the opening of the annulus or ring (or, stated otherwise, the open cross-sectional dimension of the annulus is greater than the maximal cross-sectional dimension of the body member 12 or first generally cylindrical body member), this concept includes constructions of body member 12 wherein the body member can be radially compresses to the smaller than the opening of the annulus (the result being that the annulus is larger than the compressed body member) or that the body member can somehow be manipulated to "fit through" the opening of the annulus. This concept (that the cross-sectional dimension of member 12 is smaller than the ring) also includes constructions of the annulus wherein the annulus of ring expands or enlarges such that the body member 12 can be inserted into the opening of the annulus (the result again being that the annulus is larger than the body member) or that the opening of the annulus can somehow be manipulated such that the body member can "fit through" the opening of the annulus. In any event, if the body member 12 cannot fit through the opening of the annulus, the stimulator or hanger assembly described herein could not accommodate the body member. If the body member 12 is inflatable or otherwise expandable, the deflated configuration of body member 12 is smaller than the annulus (proving the converse that the annulus opening is larger). Further, if body member 12 can be flexed or contorted and inserted into the opening of the annulus, this construct is also within the scope of the invention herein. The same is true of a flexible annulus or ring. If the ring is expandable, then the annulus opening is larger than the body member. Body member 12 includes a general cylindrical main body portion 16, a distal end 18 and a proximal end 20. Proximal end 20 is also a proximal base end having a flange element 22 extending radially from main body portion 16. Another description of the flange element 20 with respect to main body portion 16 is that flange element 22 extends normal to proximal region 24 of main body 16. Body member 12 also includes a maximal cross-sectional dimension which, in the illustrated embodiment shown in FIG. 1, may be longitudinally disposed at cross-sectional line a'-a". As discussed later in connection with FIGS. 4C and 4D, the maximal cross-sectional dimension may be at various locations along the length 1 of body member 12. Further, as discussed later in conjunction with FIG. 4B, flange element 22 may be a plurality of flange elements.

Second member 14 is generally U-shaped. Another description of second member 14 would include a truncated U-shape since bulbous end portion 30 defines a higher upward leg of U-shaped member 14 as compared with leg formed by annulus 36 at distal end 32. The U-shape may be a shallow U-shaped rather than the horseshoe shaped curve of illustrated member 14. Bulbous end portion has a cross-sectional or lateral dimension b'-b" that is larger than the cross-sectional dimension c'-c" of the stem 34 in the illustrated embodiment of FIG. 1. Bulbous end portion 30 is sized for receipt in an anal or vaginal cavity of one of the partners utilizing the two piece erogenic stimulator 10. The U-shaped member has a stem 34 which has, at its proximal end 35, the bulbous end portion 30. The distal end 32 of U-shaped member 14 has an annulus 36 which captures the phallic body member 12. Annulus 36 is disposed at terminal end 32 of second member 14. In general, annulus 36 is located or defines a plane curve d'-d" which substantially follows the curve of generally U-shaped curved stem 34. In FIG. 1, the curve of curved stem 34 is e'-e". In a different embodiment, the annulus plane curve d'-d" may be flat (an infinite radius curve) and still be considered to be substantially following the generally U-shaped curved stem 34 (U-shaped curve e'-e"). See flat plane curve annulus 36 in FIG. 5. In other words, annulus 36 falls in a flat plane and is considered to generally follow the shallow U-shaped curved stem 34. Of course, the curve of U-shaped curve stem 34 may be shallow with a larger radius and the annulus may have a larger radius of curvature than the U-shape curve or an infinite radius of curvature (flat). Annulus 36 may be a continuous ring (FIG. 3B), a ring with a gap (FIG. 3A) or a ring with flatten sides (FIG. 3B). Further, the cross-section of the annulus itself may be round (see FIG. 1 and the annulus cross-section below the cylindrical body 16) or may take any number of shapes such as a square, a rectangle, an oval, a tear-drop shape (with the narrow end of the tear drop at an inboard location relative to the opening of the annulus), a tear-drop with a truncated flat surface at the narrow end, or any other cross-sectional shape which is comfortable for the users.

Figure 3A:
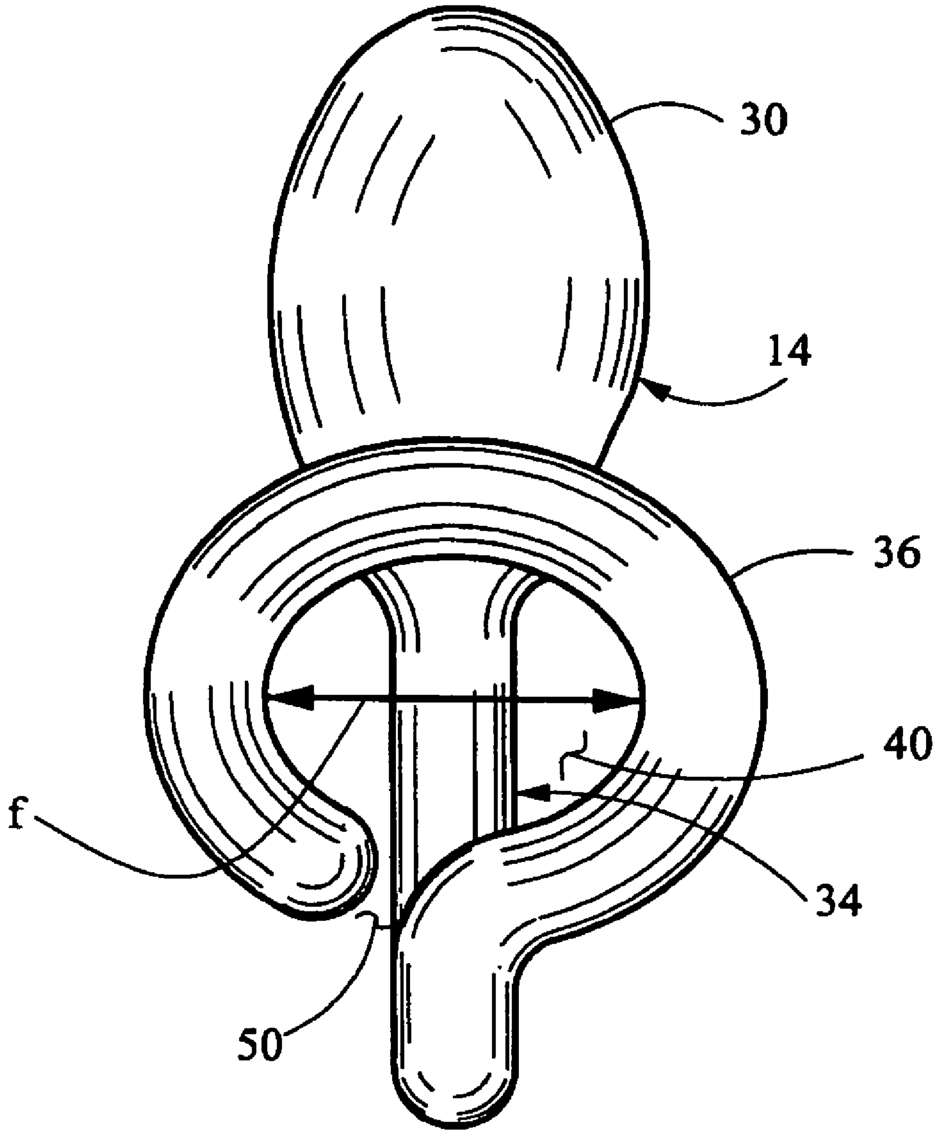
FIG. 3A is an end view of another U-shaped second member showing a discontinuity or gap in the annular ring and FIG. 3B is an end view of a further U-shaped second member showing no discontinuity or gap in the annular ring and showing a flat-sided annular ring.
Figure 3B:
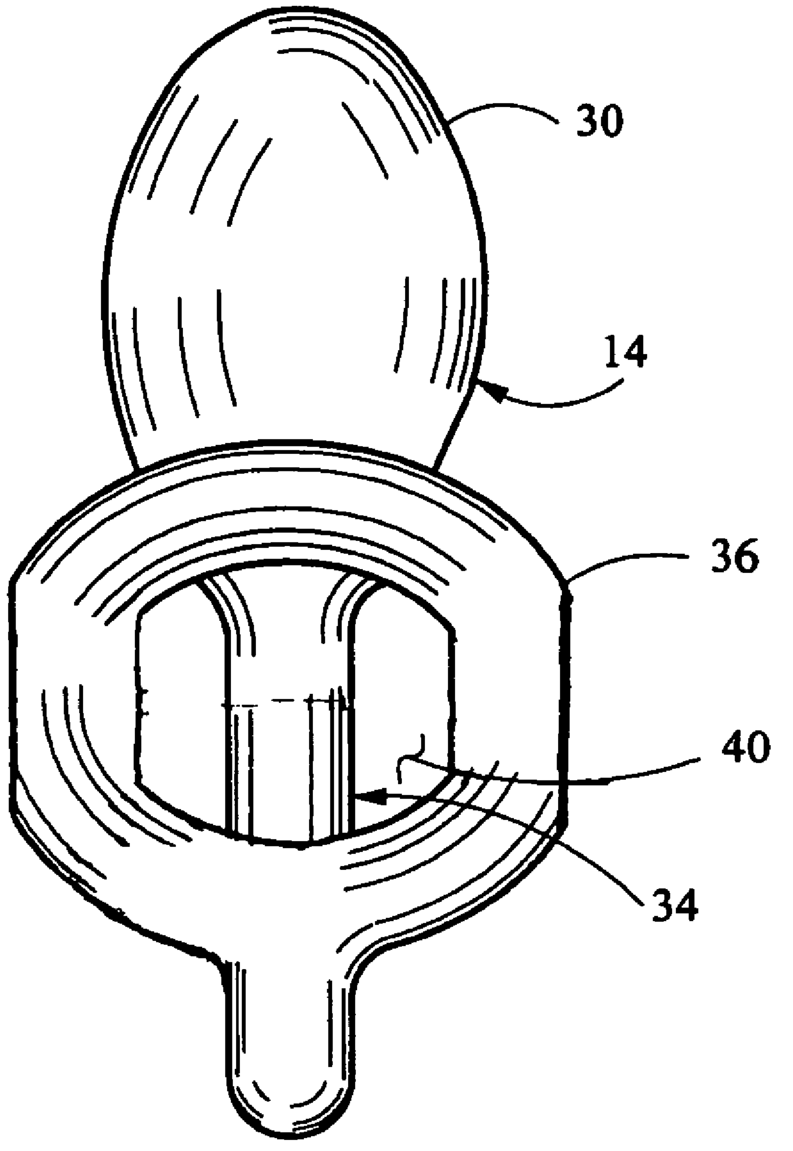

As best shown in FIG. 3A, annulus 36 has an opening 40 which has an open cross-sectional dimension F which is larger than the maximal cross-sectional dimension a'-a" of the phallic body member 12. FIG. 1 shows that flange 22 has an inboard surface 43 that abuts the inboard surface 45 of annulus 36 when the phallic body 12 is hung on annulus 36. Since the open cross-sectional dimension f of annulus 36 is larger than the maximal cross-sectional dimension a'-a" of phallic body member 12, the phallic body member 12 can be inserted into annulus 36 such that flange element 22 abuts annulus 36 and, more particularly, the inboard surface 43 of flange element 22 abuts the input inboard surface 45 of annulus 36. As used herein, the term "inboard" refers to an item that is closer to the main body portion as compared with other items. Therefore, flange 22 has an inboard surface 43 adjacent or facing main body portion 14 of phallic body member 12 and annulus 36 has an inboard surface 45 facing bulbous end portion 30. Surface or inboard faces 43, 45 may be curved rather than abrupt edge faces.

Figure 2:
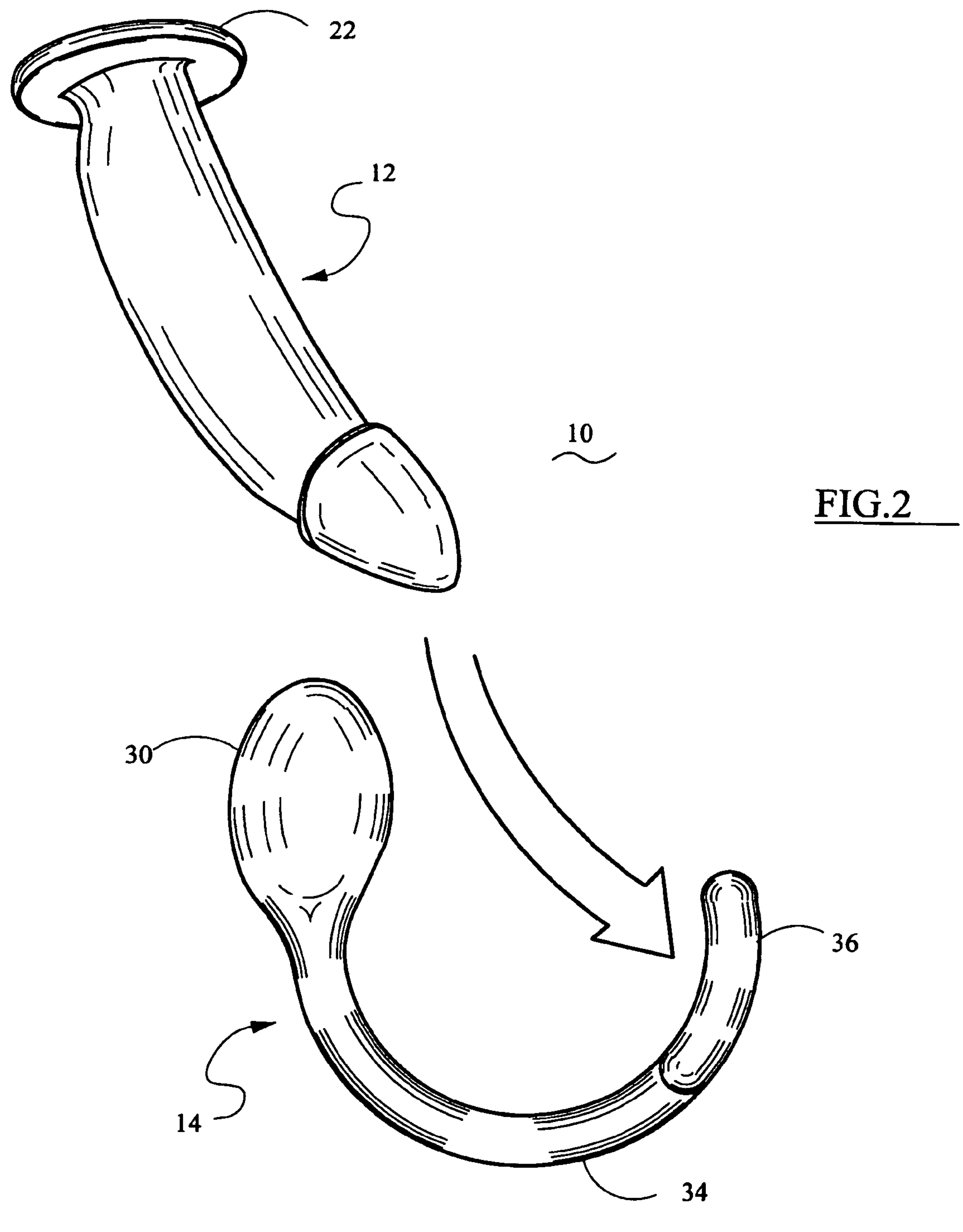
FIG. 2 diagrammatically illustrates insertion of the phallic body member into the annulus of the U-shaped second member.

FIG. 2 shows that phallic body member 12 is insertable into annulus 36 of U-shaped second member 14. As such, the erogenic stimulator 10 can be configured as a two piece erogenic stimulator for use by two partners. However, phallic body member 12 may be used independently as an erogenic stimulator and, to some degree, U-shaped second member 14 may also be used as an erogenic stimulator. The members 12, 14 are independent and separate items until body 12 is hung in annulus 36.

Alternatively, the U-shaped second body 14 may be considered a erogenic stimulator hanger 14 which is used in combination with phallic body member 12. The erogenic stimulator 14 has a generally U-shaped member with a bulbous end portion 30 sized for receipt in an anal or vaginal cavity at a distal end and a generally U-shaped curved stem 34 and an annulus or ring type member 36 at terminal end 32 of the U-shaped member 14. The annulus 36 has an opening 40 which has a cross-sectional dimension f larger than the maximal cross-sectional dimension a'-a" of the phallic body member 12. Phallic body member 12 is insertable to annulus 36 of U-shaped member 14 and, as shown in FIG. 1, the phallic body member 12 hangs from annulus 36 such that the inboard face 45 of annulus 36 abuts the inboard face 43 of flange element 22.

FIG. 3B is an end view of a further U-shaped second member showing no discontinuity or gap in the annular ring and showing a flat-sided annular ring. Additionally, FIG. 3B shows that the annular ring can have flat sides. The phallic body member 12 may also have flat sides which are complementary to the flat sided annular ring. In this manner, rotation of the phallic body member 12 with respect to the ring 36 is limited by the interlocking action of the flat sides of the phallic body member 12 and the flat sides of the annular ring 36.

FIG. 4 diagrammatically illustrates an end view of the U-shaped second member 14, sometimes referred to herein as the erogenic stimulator hanger. In the embodiment shown in FIG. 3A, annulus 36 has a discontinuity in the ring structure to form a gap 50 in the annular ring structure 36. In FIG. 3B, the ring has no gap. It should be noted that in the preferred embodiment, annulus 36 is circular however, annulus 36 may be oblong or elliptical. In this event, the various cross-sectional dimensions of annulus 36 must be larger than the maximal cross-sectional dimensions of phallic body member 12. Further, if opening 40 is elliptical and the maximal cross-sectional dimension for both elliptical axis of the phallic body member 12 is slightly smaller than the ellipse 40 of annulus 36, the matching shapes provide rotational locking action which limits rotation of phallic body member 12 with respect to U-shaped second member 14. One important aspect of the present invention is that the phallic body member 12 must be insertable into annulus 36, and the flange at the base of phallic body member 12 must limit further insertion of phallic body member 12 into annulus 36. Other aspects of the invention are discussed herein. It should be noted that the opening of the annulus or ring may take various shapes. A square shape or a polygon or triangle or oblong may be employed. See FIG. 3B. If the body member 16 has a flat face or a number of flat faces, the rotational position of the body member with respect to a designated radial line on a plane formed by the ring opening may be maintained by flat surfaces interfacing on the ring opening and the body member.

Figure 4B:
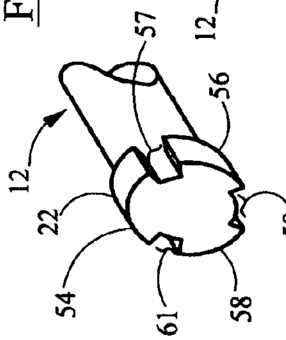
FIG. 4B diagrammatically illustrates multiple or a plurality of flange elements on the proximal base of the generally cylindrical phallic body member.
Figure 4C:
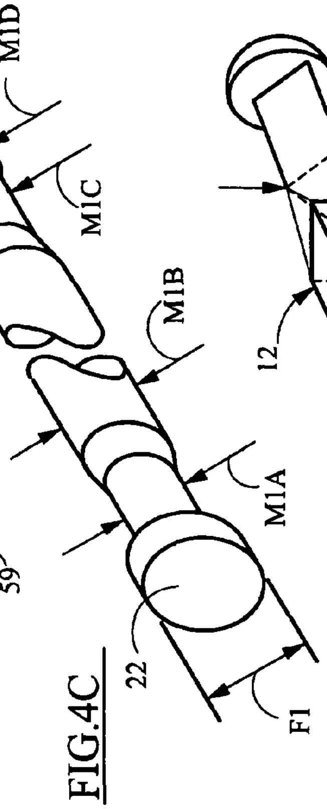
FIGS. 4C and 4D diagrammatically illustrate various cross-sectional dimensions and the maximal cross-sectional dimension of the generally cylindrical phallic body member.
Figure 4D:
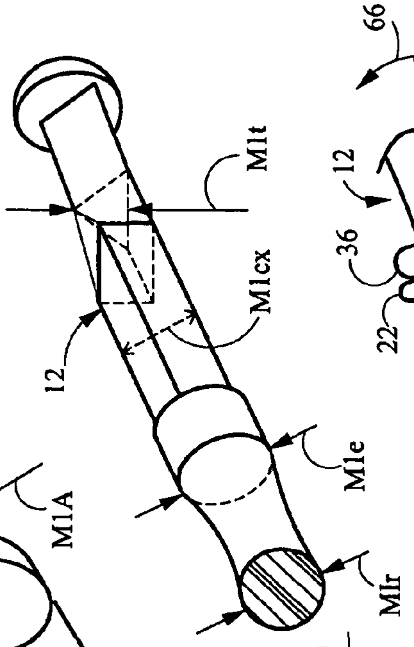
Figure 4E:
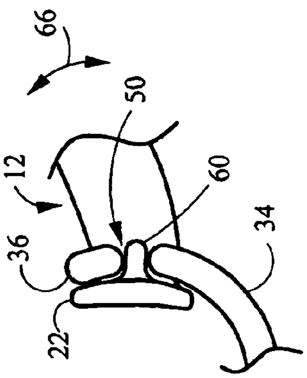
FIG. 4E diagrammatically illustrates the tab on the inboard face of the flange and the interlock with the gap on the annulus of the U-shaped second member.
Figure 4A:
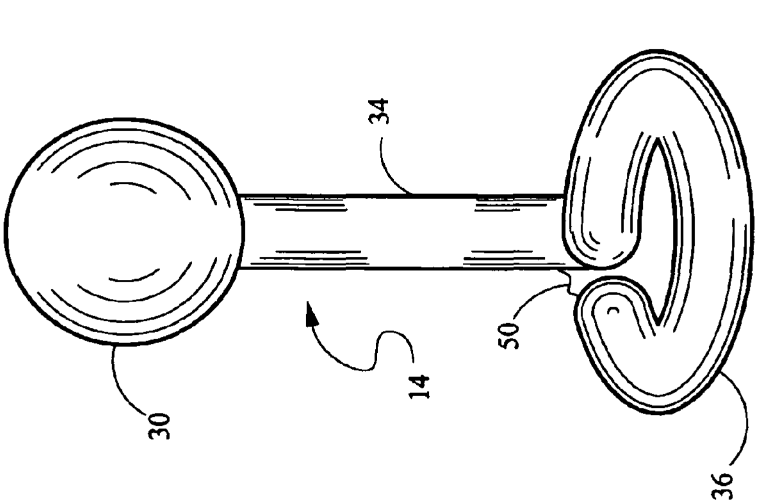
FIG. 4A is a top view of the U-shaped second member with the discontinuity.

FIG. 4A shows a top view of U-shaped member 14.

FIG. 4B diagrammatically illustrates flange element 22 consisting of a plurality of radially extending pieces 54, 56, 58. Flange elemental pieces 54, 58, 58 coact with annulus 36 such that the corresponding inboard faces of elemental flanges 54, 56, 58 limit further insertion of phallic body member 12 into annulus 36. Gaps 57, 59 and 61 space apart elemental flanges 54, 56, 58. A singular elemental flange 54 may be employed to provide the longitudinal limit or stop for member 12.

FIG. 4E diagrammatically shows flange 22 with a longitudinally extending inboard tab 60 that is complementary to gap 50 in annulus 36. In this manner, the phallic body member 12 can be rotationally locked into U-shaped second member 14 prohibiting rotation in the direction shown by double headed arrow 66 in FIG. 4E. Tab 60 locks into gap 50. Alternatively, tab 60 can protrude radially from phallic body portion 12 at a longitudinal position adjacent to but not necessarily connected to flange 22 to establish the complementary lock. A plurality of tabs may be used. The gap 50 may be vertically on the top of the annular ring 36.

FIG. 4C diagrammatically shows that phallic body member 12 may have a plurality of cross-sectional dimensions M1A, M1B, M1C and M1D. In the illustrated embodiment, the maximal cross-sectional dimension of phallic body 12 in FIG. 4C is at cross-sectional location M1B. The cross-sectional dimension of M1D is slightly smaller than M1B. The cross-sectional dimension of M1A is smaller than M1D and the cross-sectional dimension M1C which is the smallest of the entire phallic body member 12. All these cross-sectional dimensions are smaller than opening f of annulus 36 (FIGS. 1 and 3) which annulus is smaller than the cross-sectional dimension F1 of flange 22.

FIG. 4D diagrammatically illustrates phallic body 12 having various cross-sectional aspects including circular aspect M1*r*, elliptical or oval aspect M1*e*, square aspect M1*cx* and triangular aspect M1*t*. The maximal cross-sectional dimension of the ellipse or oval is its longest axis for the ellipse at M1*e*. The maximal cross-sectional dimension of the square version or section of phallic body member 12 is the diagonal dimension M1*cx*. The maximal cross-sectional dimension of the triangular section of phallic body member 12 is the geometric height M1*t* of the triangle. Therefore, the maximal cross-sectional dimension is based upon the geometry at that longitudinal position on phallic body member 12. The degree of curvature of phallic body member 12 as well as the maximal cross-sectional dimension of the body member affects insertion into annulus 36. However, one of the several important aspects of the present invention is that phallic body is insertable into annulus 36 and that inboard surface or edge 43 of flange 22 should abut inboard surface 45 of annulus 36.

Figure 6:
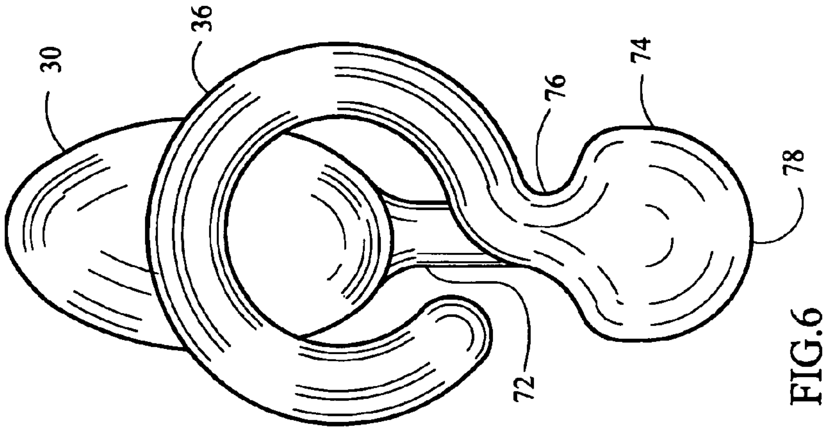
Figure 5:
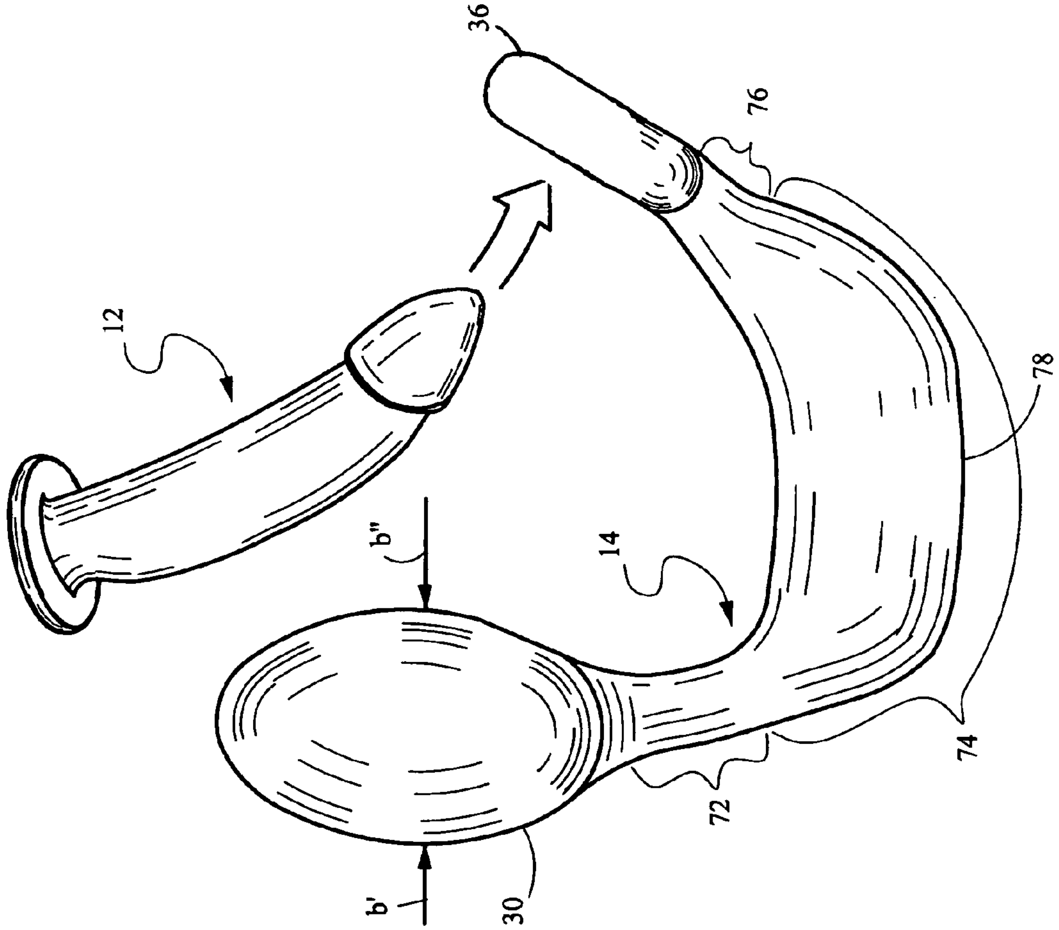
FIG. 5 diagrammatically illustrates another embodiment of the U-shaped second member; and, FIG. 6 is an end view of the U-shaped second member of FIG. 5.

FIGS. 5 and 6 show a variation of the U-shaped second member 14 with an enlarged stem mid-section. FIG. 1 shows that the cross-sectional dimension c'-c" of stem 36 is substantially uniform from bulbous end 30 to annulus 36. FIG. 5 shows a stem with three sections: proximal stem section 72, mid-section stem 74 and distal stem section 76. The cross-sectional dimension of proximal stem section 72 is substantially smaller than the cross-sectional dimension b'-b" of bulbous end 30. However, the mid-section stem 74 has an enlarged cross-sectional dimension larger than proximal section 72 and distal section 76. The enlarged mid-section 74 may sometimes be referred to as a base since the bottom region 78 may be flattened such that the U-shaped member 14 or erogenic stimulator hanger 14 can rest on its base surface 78. The difference in cross-sectional dimensions is best shown in FIG. 6. The enlarged base or mid-section permits one partner to sometimes better grip the coupled stimulators 12, 14 with thigh muscles. Base or mid-section 74 may have a wider lateral cross-section compared to the loop end 36 and/or compared to the bulbous end 30. Base or mid-section 74 may have a smaller lateral cross-section compared to the loop end 36 and/or compared to the bulbous end 30. In a similar manner, the lateral cross-sectional dimension of base or mid-section 74 may be equal to either the lateral cross-sectional dimension of either loop end 36 or bulbous end 30. See flat plane curve annulus 36 in FIG. 5.

In one embodiment, cylindrical phallic body 12 is somewhat resilient. In another embodiment, the U-shaped member is resilient. Various combination of materials and flexibility may be employed. The annular ring (FIG. 3A, 3B) material may be silicone, vinyl or plastic.

With respect to the U-shaped second member 14, the reduced cross-sectional dimension of stem 34 compared to the larger cross-sectional dimension of bulbous end 30 enables the user to better retain bulbous end in the body cavity. Bulbous end 30 is adopted to permit the muscle groups of one of the partners using the erogenic stimulator to hold the U-shaped member in place during use. As explained earlier, the opening 40 of annulus 36 may take a variety of shapes including circle, oval, ellipse, triangle, square, polygon, rectangular or diamond shapes. However, the maximal cross-sectional dimension of phallic number 12 must be less than the maximal opening dimension of the shape of annulus 36. Complementary shapes of the open space of annulus 36 and body 12 are alternate embodiments of the invention. The ring opening must be larger than sections of the phallic body. Complementary shapes provide rotational locking action for members 12, 14.

In operation, the phallic member 12 is inserted into annulus 36 such that the distal end 18 of phallic member 12 extends outboard beyond annulus 36 and flange 22 abuts annulus 36. Thereafter, one partner places bulbous end 30 in an anal or vaginal cavity and the phallic body member 12 is inserted into an anal or vaginal cavity of the other partner.

Various materials may be utilized for the phallic body member 12 and the U-shaped member 14. Since the erogenic stimulator is a two piece construction, different materials may be used for members 12, 14. The actual length and diameter of the phallic body member 12 and the bulbous end 30 of U-shaped member 14 can vary dependent on the needs and desires of the partners. Therefore, the illustrated sizes are examples of various different sizes of various members 12, 14. Further, the shape and radius and other dimensions of the curved U-shape member may be larger or smaller.

The stem portion body 74 (FIG. 5) may include grooves, bumps, chevrons, ridges or other shape deviations on the inside of the U-shaped stem, near end region 76 (but inboard of the U-shape) to stimulate the user carrying the bulb 30 in her vagina.

The claims appended hereto are meant to cover modifications and changes within the scope and spirit of the present invention.

What is claimed is:

1. A two-piece erogenic stimulator for use by two partners comprising:

a first elongated generally cylindrical and phallic body member having a distal member end and a proximal base end, said generally cylindrical body member having a maximal cross-sectional dimension, said proximal base end having a flange element extending radially from said body member;

a second member having a bulbous first end portion sized for receipt in an anal or vaginal cavity and said second member having a generally U-shaped curved stem leading from said bulbous first end portion to a distal second member end, said distal second end having an annulus at a terminal end of said second member, said annulus defining a plane curve which substantially follows said generally U-shaped curved stem;

said annulus defining an opening with an open cross-sectional dimension greater than said maximal cross-sectional dimension of said first generally cylindrical body member; and said first generally cylindrical body member and said second member having a coupled mode and an uncoupled mode, in said coupled mode, said first generally cylindrical body member inserted through said annulus of said second member such that an inboard face of said annulus abuts an inboard face of said flange element of said first cylindrical body member and said distal member end thereof extends away from said bulbous end portion of said second member, and in an uncoupled mode, said first and second members are structurally separate, disassociated pieces.

2. A two-piece stimulator as claimed in claim 1 wherein said first generally cylindrical body member is resilient.

3. A two-piece stimulator as claimed in claim 1 wherein said second member is resilient.

4. A two-piece stimulator as claimed in claim 1 wherein said flange element at said proximal base end of said first generally cylindrical body member is at a terminus of said first body member.

5. A two-piece stimulator as claimed in claim 1 wherein said annulus is at a terminus of said stem of said second member.

6. A two-piece stimulator as claimed in claim 1 wherein said bulbous end portion of said second member has a bulbous cross-sectional dimension and said stem has a stem cross-sectional dimension, said bulbous cross-sectional dimension begin greater than said stem cross-sectional dimension.

7. A two-piece stimulator as claimed in claim 1 wherein said U-shaped curved stem is a shallow U-shaped curved stem.

8. A two-piece stimulator as claimed in claim 7 wherein said annulus defines a flat plane curve and said flat plane curve annulus substantially follows said shallow U-shaped curved stem.

9. A two-piece stimulator as claimed in claim 1 wherein said second member is rigid and said first generally cylindrical body member is resilient.

10. A two-piece stimulator as claimed in claim 1 wherein said flange includes a plurality of flange elements, each of said plurality of flange elements extending radially from said first body member.

11. A two-piece stimulator as claimed in claim 1 wherein said annulus defines a discontinuity thereat, said discontinuity forming a gap in said annulus.

12. A two-piece stimulator as claimed in claim 11 wherein said flange includes a tab complementary to said gap in said annulus.

13. A two-piece stimulator as claimed in claim 1 wherein said stem has a substantially inform cross-sectional dimension.

14. A two-piece stimulator as claimed in claim 1 wherein said stem has a proximal end adjacent said bulbous end portion, an enlarged midsection and a distal end adjacent said annulus, said enlarged stem midsection having one or both of:

a larger cross-sectional dimension than a cross-sectional dimension of said proximal end of said stem, and a larger cross-sectional dimension than a cross-sectional dimension of said distal end of said stem.

15. A two-piece stimulator as claimed in claim 4 wherein said bulbous end portion of said second member has a bulbous cross-sectional dimension and said stem has a stem cross-sectional dimension, said bulbous cross-sectional dimension being greater than said stem cross-sectional dimension.

16. A two-piece stimulator as claimed in claim 15 wherein said U-shaped curved stem is a shallow U-shaped curved stem and said plane curve of said annulus is either a flat plane curve which substantially follows said shallow U-shaped curved stem or said plane curve of said annulus is slightly curved to identically follow said shallow U-shaped curve of said curved stem.

17. A two-piece stimulator as claimed in claim 16 wherein said flange includes a plurality of flange elements, each of said plurality of flange elements extending radially from said first body member.

18. A two-piece stimulator as claimed in claim 17 wherein said annulus defines a discontinuity thereat, said discontinuity forming a gap in said annulus.

19. A two-piece stimulator as claimed in claim 18 wherein said flange includes a tab complementary to said gap in said annulus.

20. A two-piece stimulator as claimed in claim 19 wherein said stem has a proximal end adjacent said bulbous end portion, an enlarged midsection and a distal end adjacent said annulus, said enlarged stem midsection having one or both of a larger cross-sectional dimension than a cross-sectional dimension of said proximal end of said stem, and a larger cross-sectional dimension than a cross-sectional dimension of said distal end of said stem.

21. An erogenic stimulator hanger in combination with a first elongated generally cylindrical phallic body member having a distal first member end and a proximal base end, said generally cylindrical body member having a maximal cross-sectional dimension, said proximal base end having a flange element extending radially from said phallic body member and having an inboard face facing said distal first member end; the coupled erogenic stimulator hanger and said phallic body member for use by two partners, the erogenic stimulator hanger comprising:

a generally U-shaped member having, at one end, a bulbous end portion sized for receipt in an anal or vaginal cavity and said U-shaped member having a generally U-shaped curved stem leading from said bulbous end portion to a distal end remote from said bulbous end portion, said distal end having an annulus at a terminal end of said U-shaped member, said annulus defining a plane curve which substantially follows said generally U-shaped curved stem;

said annulus defining an opening with an open cross-sectional dimension greater than said maximal cross-sectional dimension of said phallic body member such that said generally cylindrical body member of said phallic body member is insertable through said annulus of said U-shaped member and hangs from said annulus with an inboard face of said annulus abutting said inboard face of said flange element.

22. An erogenic stimulator hanger in combination with a phallic body member as claimed in claim 21 wherein said bulbous end portion of said U-shaped member has a bulbous cross-sectional dimension and said stem has a stem cross-sectional dimension, said bulbous cross-sectional dimension begin greater than said stem cross-sectional dimension.

23. An erogenic stimulator hanger in combination with a phallic body member as claimed in claim 22 wherein said U-shaped curved stem is a shallow U-shaped curved stem and said plane curve of said annulus is either a flat plane curve which substantially follows said shallow U-shaped curved stem or said plane curve of said annulus is slightly curved to identically follow said shallow U-shaped curve of said curved stem.

24. An erogenic stimulator hanger in combination with a phallic body member as claimed in claim 23 wherein said flange includes a tab extending distally from said inboard face of said flange and wherein said annulus defines a discontinuity thereat, said discontinuity forming a gap in said annulus and said flange tab is complementary to said gap in said annulus when said phallic body member is hung on said annulus.

25. An erogenic stimulator hanger in combination with a phallic body member as claimed in claim 24 wherein said stem has a proximal end adjacent said bulbous end portion, an enlarged midsection and a distal end adjacent said annulus, said enlarged stem midsection having one or both of:

a larger cross-sectional dimension than a cross-sectional dimension of said proximal end of said stem, and a larger cross-sectional dimension than a cross-sectional dimension of said distal end of said stem.

26. An erogenic stimulator hanger in combination with a phallic body member as claimed in claim 21 wherein said U-shaped curved stem is a shallow U-shaped curved stem and said plane curve of said annulus is either a flat plane curve which substantially follows said shallow U-shaped curved stem or said plane curve of said annulus is slightly curved to identically follow said shallow U-shaped curve of said curved stem.

27. An erogenic stimulator hanger in combination with a phallic body member as claimed in claim 21 wherein said flange includes a tab extending distally from said inboard face of said flange and wherein said annulus defines a discontinuity thereat, said discontinuity forming a gap in said annulus and said flange tab is complementary to said gap in said annulus when said phallic body member is hung on said annulus.

28. An erogenic stimulator hanger in combination with a phallic body member as claimed in claim 21 wherein said stem has a proximal end adjacent said bulbous end portion, an enlarged midsection and a distal end adjacent said annulus, said enlarged stem midsection having one or both of:

a larger cross-sectional dimension than a cross-sectional dimension of said proximal end of said stem, and a larger cross-sectional dimension than a cross-sectional dimension of said distal end of said stem.

29. An erogenic stimulator hanger in combination with a first elongated generally cylindrical phallic body having a distal body end and a proximal body base end, said generally cylindrical phallic body having a maximal cross-sectional dimension, said proximal body base end having one or more flange elements extending radially from said phallic body with corresponding inboard faces; said phallic body member coupled and hung on the erogenic stimulator hanger for use by two partners and the erogenic stimulator hanger comprising:

a generally U-shaped member having a bulbous end portion sized for receipt in an anal or vaginal cavity and a curved stem leading from said bulbous end portion to an annulus forming a distal end portion of said generally U-shaped curve;

said annulus defining an opening with an open cross-sectional dimension greater than said maximal cross-sectional dimension of said phallic body member such that said phallic body is insertable through said annulus and hangs thereon when an inboard face of said annulus abuts said inboard face of said one or more flange elements.

30. A two-piece erogenic stimulator for use by two partners comprising:

a first elongated generally cylindrical and phallic body member having a distal member end and a proximal base end, said generally cylindrical body member having a body cross-sectional shape, said proximal base end having a flange element extending radially from said body member;

a second member having a bulbous end portion sized for receipt in an anal or vaginal cavity and said second member having a generally U-shaped curved stem portion leading from said bulbous end portion to a distal second member end, said distal second end having an annulus at a terminal end of said second member, said annulus defining a plane curve which substantially follows said generally U-shaped curved stem portion;

said annulus defining an opening with an open cross-sectional shape which is complementary to said body cross-sectional shape of said first generally cylindrical body member; and said first generally cylindrical body member and said second member having a coupled mode and an uncoupled mode, in said coupled mode, said first generally cylindrical body member inserted through said annulus of said second member such that an inboard face of said annulus abuts an inboard face of said flange element of said first cylindrical body member and said distal member end thereof extends away from said bulbous end portion of said second member, and in an uncoupled mode, said first and second members are structurally separate, disassociated pieces.

31. A two-piece stimulator as claimed in claim 1 wherein said bulbous end portion has a maximal cross-sectional dimension and said annulus has a maximal cross-sectional dimension, and wherein said stem has a proximal end adjacent said bulbous end portion, an enlarged midsection and a distal end adjacent said annulus, said enlarged stem midsection having one or both of:

a smaller cross-sectional dimension than a cross-sectional dimension of said bulbous end; and a smaller cross-sectional dimension than a cross-sectional dimension of said annulus.

32. A erogenic stimulator hanger as claimed in claim 21 wherein said bulbous end portion has a maximal cross-sectional dimension and said annulus has a maximal cross-sectional dimension, and wherein said stem has a proximal end adjacent said bulbous end portion, an enlarged midsection and a distal end adjacent said annulus, said enlarged stem midsection having one or both of:

a smaller cross-sectional dimension than a cross-sectional dimension of said bulbous end; and a smaller cross-sectional dimension than a cross-sectional dimension of said annulus.

33. A two-piece stimulator as claimed in claim 1 wherein said bulbous end portion has a maximal cross-sectional dimension and said annulus has a maximal cross-sectional dimension, and wherein said stem includes one of:

an enlarged midsection;

an enlarged midsection intermediate a smaller proximal stem end adjacent said bulbous end portion and a smaller distal stem end adjacent said annulus;

an enlarged midsection having a maximal cross-sectional dimension which is either larger or smaller than said cross-sectional dimension of said bulbous end portion;

an enlarged midsection having a maximal cross-sectional dimension which is either larger or smaller than said maximal cross-sectional dimension of said annulus; and, an enlarged midsection having a maximal cross-sectional dimension which is substantially the same size as said maximal cross-sectional dimension of said annulus.

34. A erogenic stimulator hanger as claimed in claim 21 wherein said bulbous end portion has a maximal cross-sectional dimension and said annulus has a maximal cross-sectional dimension, and wherein said stem includes one of:

an enlarged midsection;

an enlarged midsection intermediate a smaller proximal stem end adjacent said bulbous end portion and a smaller distal stem end adjacent said annulus;

an enlarged midsection having a maximal cross-sectional dimension which is either larger or smaller than said cross-sectional dimension of said bulbous end portion;

an enlarged midsection having a maximal cross-sectional dimension which is either larger or smaller than said maximal cross-sectional dimension of said annulus; and, an enlarged midsection having a maximal cross-sectional dimension which is substantially the same size as said maximal cross-sectional dimension of said annulus.

* * * * *